US009689801B2

(12) United States Patent
Kho et al.

(10) Patent No.: US 9,689,801 B2
(45) Date of Patent: Jun. 27, 2017

(54) SERS-BASED ANALYTE DETECTION

(75) Inventors: Kiang Wei Kho, Singapore (SG); Olivo Malini, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 117 days.

(21) Appl. No.: 13/517,937

(22) PCT Filed: Dec. 16, 2010

(86) PCT No.: PCT/SG2010/000472
§ 371 (c)(1),
(2), (4) Date: Oct. 12, 2012

(87) PCT Pub. No.: WO2011/078794
PCT Pub. Date: Jun. 30, 2011

(65) Prior Publication Data
US 2013/0023435 A1    Jan. 24, 2013

Related U.S. Application Data

(60) Provisional application No. 61/289,053, filed on Dec. 22, 2009.

(51) Int. Cl.
*G01N 21/65* (2006.01)
*G01N 33/553* (2006.01)
*G01N 33/532* (2006.01)
*G01N 33/543* (2006.01)
*G01N 33/58* (2006.01)

(52) U.S. Cl.
CPC ......... *G01N 21/658* (2013.01); *G01N 33/532* (2013.01); *G01N 33/54373* (2013.01); *G01N 33/553* (2013.01); *G01N 33/58* (2013.01)

(58) Field of Classification Search
CPC .......... G01N 21/658; G01N 33/54373; G01N 33/553; G01N 33/532; G01N 33/58
See application file for complete search history.

(56) References Cited

U.S. PATENT DOCUMENTS 4,376,110 A    3/1983    David et al.
4,946,778 A    8/1990    Ladner et al.
(Continued)

FOREIGN PATENT DOCUMENTS

CN    1930475 A    3/2007
CN    1934438 A    3/2007
(Continued)

OTHER PUBLICATIONS

Grubisha et al 2003 Analytical Chemistry 75: 5936-5943.*
(Continued)

*Primary Examiner* — Jeremy C Flinders
(74) *Attorney, Agent, or Firm* — Wolf, Greenfield & Sacks, P.C.

(57) ABSTRACT

The present invention relates to method detecting analytes by surface enhanced Raman spectroscopy (SERS), comprising contacting the analytes with at least one analyte binding molecule attached to a metal substrate surface that enhances Raman scattering via a Raman-active molecular linker; and detecting a surface enhanced Raman signal from said compound. In a further aspect, this invention relates to a conjugate and a biosensor suitable for the invented SERS-based analyte detection method.

13 Claims, 18 Drawing Sheets

(56) References Cited

U.S. PATENT DOCUMENTS

| | | |
|---|---|---|
| 6,682,736 B1 | 1/2004 | Hanson et al. |
| 2003/0059820 A1 | 3/2003 | Vo-Dinh |
| 2003/0211488 A1 | 11/2003 | Mirkin et al. |
| 2005/0089901 A1* | 4/2005 | Porter .................... C07H 21/02 435/6.11 |
| 2005/0089932 A1 | 4/2005 | Kolkman et al. |
| 2005/0191665 A1* | 9/2005 | Su et al. ............................ 435/6 |
| 2006/0046313 A1 | 3/2006 | Roth et al. |
| 2006/0147941 A1* | 7/2006 | Su .......................... B82Y 30/00 435/6.11 |
| 2007/0058165 A1 | 3/2007 | Mondello |
| 2007/0059203 A1 | 3/2007 | Burrell et al. |

FOREIGN PATENT DOCUMENTS

| | | |
|---|---|---|
| EP | 2 040 075 A1 | 3/2009 |
| WO | WO-99/16873 A1 | 4/1999 |
| WO | WO-00/75308 A1 | 12/2000 |
| WO | WO-03/029462 A1 | 4/2003 |
| WO | WO-03/029463 A2 | 4/2003 |
| WO | WO-03/029471 A1 | 4/2003 |
| WO | WO-2005/019254 A1 | 3/2005 |
| WO | WO-2005/019255 A1 | 3/2005 |
| WO | WO-2005/019256 A2 | 3/2005 |
| WO | WO 2005098441 A2 * | 10/2005 |
| WO | WO-2007/059514 A2 | 5/2007 |
| WO | WO-2007/059514 A8 | 5/2007 |
| WO | WO-2009/040114 A2 | 4/2009 |
| WO | WO-2009/040114 A3 | 4/2009 |
| WO | WO-2011/078794 A1 | 6/2011 |
| WO | WO-2012/102681 A1 | 8/2012 |

OTHER PUBLICATIONS

Mantelingu et al 2007 J Phys Chem B 111: 4527-4534.*
International Search Report and Written Opinion for PCT/SG2010/000472 mailed Feb. 28, 2011.
International Preliminary Report for Patentability for PCT/SG2010/000472 mailed Oct. 26, 2011.
Albrecht et al., Anomalously Intense Raman Spectra of Pyridine at a Silver ElectrodeJ. Am. Chem. Soc. Jul. 20, 1977;99 (15):5215-7.
Baker et al., Progress in plasmonic engineering of the surface-enhanced Raman-scattering substrates toward ultra-trace analysis. Anal Bioanal Chem. Jul. 28, 2005;382:1751-70.
Berger et al., Surface stress in the self-assembly of alkanethiols on gold. Sci. Jun. 27, 1997;276:2021-2024.
Chen et al., Can molecular dynamics simulations provide high-resolution refinement of protein structure? Prot. Mar. 20, 2007;67(4):922-30.
Fleischman et al., Raman spectra of pyridine adsorbed at a silver electrode. Chem Phys Lett. May 15, 1974;26 (2):163-6.
Garman., X-ray data collection from macromolecular crystals. Methods Mol Biol. 2007;The 364:63-94. (The year of publication is sufficiently earlier than the effective U.S. filing date and any foreign priority date so that the particular month of publication is not an issue. See MPEP 609.04(a)).
Gold et al., Demonstration of tumor-specific antigens in human colonic carcinomata by immunological tolerance and absorption techniques. J Exp Med. Mar. 1, 1965;121:439-71.
Hagan et al., Nanomechanical forces generated by surface grafted DNA. J Phys Chem B. Jun. 9, 2002;106(39):10163-73.
Haynes et al., Plasmon-sampled surface-enhanced raman excitation spectroscopy. J Phys Chem B. Mar. 29, 2003;107(30):7426-33.
Hood et al., Systems biology and new technologies enable predictive and preventative medicine. Sci. Oct. 22, 2004;306:640-3.
Jeanmaire et al., Surface raman spectroelectrochemistry. Part I. heterocyclic, aromatic, and alphatic amines adsorbed on the anodized silver electrode. J Electroanal Chem. 1977;84(1):1-20. (The year of publication is sufficiently earlier than the effective U.S. filing date and any foreign priority date so that the particular month of publication is not an issue. See MPEP 609.04(a)).
Kauffman et al., Electronically monitoring biological interactions with carbon nanotube field-effect transistors. Chem Soc Rev. Apr. 7, 2008;37:1197-1206.
Kelly et al., The optical properties of metal nanoparticles: the influence of size, shape, and dielectric environment. J Phys Chem B. Dec. 21, 2003;107(3):668-77.
Kneipp et al., Ultrasensitive chemical analysis by raman spectroscopy. Chem Rev. Sep. 28, 1999;99(10):2957-75.
Lemarchand et al., A radio-immunoasay for the determination of thyroid stimulating hormone. Experientia. 1965;21(6):353-6. (The year of publication is sufficiently earlier than the effective U.S. filing date and any foreign priority date so that the particular month of publication is not an issue. See MPEP 609.04(a)).
Levenson, Biomarkers for early detection of breast cancer: what, when, and where? Biochimica et Biophysic Acta. Feb. 12, 2007;177:847-56.
Liang et al., Chemical effect of SERS with near-infrared excitation. J Raman Spectro. 1996;27(12):879-85. (The year of publication is sufficiently earlier than the effective U.S. filing date and any foreign priority date so that the particular month of publication is not an issue. See MPEP 609.04(a)).
Moskovits, Surface-enhanced raman spectroscopy: a brief retrospective. J Raman Spectro. 2005;36(6-7):485-96. (The year of publication is sufficiently earlier than the effective U.S. filing date and any foreign priority date so that the particular month of publication is not an issue. See MPEP 609.04(a)).
Pieczonka et al., Single Molecule analysis by surface-enhanced Raman scattering. Chem Soc Rev. 2008; 37:946-54. Epub Feb. 27, 2008.
Nishihira et al., Detection of biomolecule by aptamer beacon. Nucleic Acids Symp. 2004;48:135-6. (The year of publication is sufficiently earlier than the effective U.S. filing date and any foreign priority date so that the particular month of publication is not an issue. See MPEP 609.04(a)).
Raman et al., A New Type of Secondary Radiation. Nature. Mar. 31, 1928;121(3048):501-2.
Schlucker et al., Immuno-raman microspectroscopy: in situ detection of antigens in tissue specimens by surface-enhanced raman scattering. J Raman Spectroscopy. Apr. 10, 2006:37:719-21.
Vo-Dinh, Surface-enhanced raman spectroscopy using metallic nanostructures. Anal. Chem. 1998;17(8-9):557-82. Nishihira et al., Detection of biomolecule by aptamer beacon. Nucleic Acids Symp Ser. 48. 2004: 135-6. (The year of publication is sufficiently earlier than the effective U.S. filing date and any foreign priority date so that the particular month of publication is not an issue. See MPEP 609.04(a)).
Waggoner et al., Micro- and nanomechanical sensors for environmental, chemical, and biological detection. Lab Chip. Jul. 25, 2007;7:1238-55.
Wu et al., Origin of nanomechanical cantilever motion generated from biomolecular interactions. PNAS. Feb. 12, 2001;98(4):1560-4.
Yonzon et al., Localized surface plasmon resonance immunoassay and verification using surface-enhanced raman spectroscopy. Proceedings of SPIE. 2003;5224:78-85. Nishihira et al., Detection of biomolecule by aptamer beacon. Nucleic Acids Symp Ser. 48. 2004: 135-6. (The year of publication is sufficiently earlier than the effective U.S. filing date and any foreign priority date so that the particular month of publication is not an issue. See MPEP 609. 04(a)).
Kneipp et al., Detection and identification of a single DNA base molecule using surface-enhanced Raman scattering (SERS). Physical Review E. Jun. 1998;57(6):R6281-4.
Extended European Search Report mailed May 8, 2013 for EP10839909.8.
CN201080059252.1, Mar. 28, 2014, Office Action.

* cited by examiner

SERS-BASED ANALYTE DETECTION

CROSS-REFERENCE TO RELATED APPLICATIONS

This application is a US national stage application based on International Application No. PCT/SG2010/000472, filed 16 Dec. 2010, which claims the benefit of priority of US provisional application No. 61/289,053, filed 22 Dec. 2009, the contents of each of which are hereby incorporated by reference in their entireties for all purposes.

FIELD OF THE INVENTION

The present invention lies in the field of spectroscopy and molecular diagnostics and relates to method detecting analytes by surface enhanced Raman spectroscopy (SERS) by spectroscopically detecting antigen/antibody binding events. In particular, the invention is directed to a method for the detection of analytes using surface enhanced Raman spectroscopy (SERS), comprising contacting the analytes with at least one analyte binding molecule attached to a metal substrate surface that enhances Raman scattering via a Raman-active molecular linker; and detecting a surface enhanced Raman signal from said compound. In a further aspect, this invention relates to a conjugate and a biosensor suitable for the invented SERS-based analyte detection method.

BACKGROUND

In medical practice, identification of a disease requires not just recognition of the symptoms but also detecting specific features that would unambiguously indicate its presence. Furthermore, an early detection in asymptomatic populations is of utmost importance not only to facilitate early treatment but also to reduce health-care costs.

Usually, screening for signs of disease developments, biomarkers, is only conceivable through an analysis of biological fluids, such as blood, urine and cerebral spinal fluid, for circulating disease-related biomarkers. An accurate diagnostic can rarely be accomplished through the detection of just one single biomarker and a panel of markers has to be analyzed for a reliable results, such as in a multiplexed assay. Furthermore, monitoring the expression patterns of a variety of biomarkers at various stages of a disease could not only assist prognosis, but also allow one to follow disease progression.

Today, most protein biomarker assays are based on immunoassays. These usually provide a platform, made of either polymer or glass, bearing several immobilized antibodies spotted on different well-defined locations. These assays involve exposure of the platform to the sample followed by incubation with one or two further antibodies and several washing and blocking steps in between to increase the specificity of the assay results. Detection is usually via fluorescence detection, chromophoric absorption or a colorimetric readout. Importantly, conventional immunoassays (i.e. ELISA and fluorescent immunoassay) have limited expandability in terms of the number of proteins that can be detected per assay. This is attributed to the limited number of sensing area that can be incorporated within a single assay platform, due to the minimum laser spot-size achievable in the read-out system because of diffraction-limit, which impose a lower-limit to the useful size of a sensing area to a value not smaller than 200 nm, though in practice the size is usually in the range of 1 μm. Although one may argue that it is possible to modify a fluorescent immunoassay to allow multiple analytes (i.e. proteins/biomarkers) to be simultaneously detected by incorporating more than one fluorophore into each sensing area—for example, by expanding the number of protein-capturing fluorescent beacons used per sensing area, the broad fluorescence bandwidths (60-90 nm) unfortunately limit the maximum number of detectable fluorophores per sensing area to about 3. In other words, the maximum number of proteins detectable for each sensing area in a conventional immunoassay cannot exceed 3. Although, many immunosensor arrays have been developed in recent years, a truly rapid, accurate and miniaturizable system is still non-existing.

Vibrational spectroscopic techniques namely infra red (IR), normal Raman and Surface Enhanced Raman (SER) have been considered for analyte detection. Since near IR and mid IR technique suffers with the limitation of competing absorption from aqueous media, Raman spectroscopic techniques have evolved as the methods of choice. One important aspect of the Raman scattering is the correlation between the amount of the frequency shifts and the vibrational modes of the molecules. Since vibrational modes are sensitive to the chemical nature of the molecule, probing molecular vibrations can thus reveal information regarding its chemical geometry and interaction with other molecules. While a plethora of techniques, such as nuclear magnetic resonance (NMR) and X-ray crystallography, can also provide access to chemical structures, optical measurements of vibrational states via Raman scattering offer, owing to the ease of sample preparation, a much more convenient approach. For this reason, the Raman spectrum, which is unique to each molecule, has been utilized as a "fingerprint" in identifying unknown species, and in a more interesting aspect, Raman scattering is utilized for elucidating conformational changes.

However, under biological conditions the applications have been limited mainly due to the poor sensitivity and the need for high laser power and complicated instrumentation.

Most of these drawbacks were overcome by the development of Surface Enhanced Raman spectroscopy (SERS) where the spectral intensity is enhanced tremendously by the interaction of the SERS active analyte molecules with a substrate surface, e.g., a nanoparticle surface of copper, gold or silver. There are many cases where these enhancement factors are up to the level of single molecule detection (Nicholas & Ricardo, *Chem. Soc. Rev.*, 2008, 37, 946-954). However, the detection of molecules with such extraordinary sensitivity still depends on the properties of the molecule-nanoparticle ensemble and is currently limited to certain classes of SERS active molecules.

SUMMARY OF THE INVENTION

The present invention allows the expansion of an SERS-based detection to a highly multiplexed system capable of detecting multiple proteins per sensing area. In contrast to immunoassays, no secondary or tertiary antibodies are required for the detection, hence minimizing material wastage. Furthermore, the invention requires neither colored substance nor extrinsic labeler as it is based on the detection of a molecular fingerprint.

In an additional aspect, the inventive assay design does not require multiple washing steps. In fact, no or only one washing step is sufficient to achieve detection In a first aspect, the present invention thus relates to a method for detecting one or more analytes using surface enhanced Raman spectroscopy (SERS), the method including:

contacting the one or more analytes with at least one analyte binding molecule attached to a metal substrate surface that enhances Raman scattering via a Raman-active molecular linker; and detecting a surface enhanced Raman signal from said compound.

In various embodiments of this method the surface enhanced Raman signal of the compound is correlated with the amount of the analytes. The analytes may be contained in a sample and the detection may be in vitro. In one embodiment of the invented method, the analytes are detected in a bodily fluid comprising said analyte. The bodily fluid may be selected from the group consisting of plasma, serum, blood, lymph, liquor and urine.

In various embodiments of the claimed methods, the analyte is a protein, peptide, nucleic acid, carbohydrate, lipid, cell, virus, small molecule, or hapten.

In one embodiment, the analyte binding molecule specifically binds the analyte. The analyte binding molecule may be selected from the group consisting of an antibody, antibody fragment or antibody like molecules. If the analyte binding molecule is an antibody, the antibody may be a monoclonal or polyclonal antibody.

The method may also be a multiplex method for detecting more than one analyte, wherein in the contacting step more than one analyte binding molecules are used.

In various embodiments of the method, the analyte binding molecule is covalently coupled to a Raman-active molecular linker that is attached to the substrate surface via covalent interactions. The Raman-active molecular linker compound may be selected from the group consisting of 6-Mercaptopurine, 8-Aza-adenine, N-Benzoyladenine, 2-Mercapto-benzimidazole, 4-Amino-pyrazole[3,4-d]pyrimidine, Zeatin, Methylene Blue, 9-Amino-acridine, Ethidium Bromide, Bismarck Brown Y, N-Benzyl-aminopurine, Thionin acetate, 3,6-Diaminoacridine, 6-Cyanopurine, 4-Amino-5-imidazole-carboxamidehydrochloride, 1,3-Diiminoisoindoline, Rhodamine 6G, Crystal Violet, Basic Fuchsin, Aniline Blue Diammonium salt, N-[(3-(Anilinomethylene)-2-chloro-1-cyclohexen-1-yl)methylene]anilinemonohydrochloride, O-(7-Azabenzotriazol-1-yl)-N,N, N',N'-tetramethyluroniumhexafluorophosphate, 9-Aminofluorene hydrochloride, Basic Blue, 1,8-Diamino-4,5-dihydroxyanthraquinone, Proflavine hemisulfate salt hydrate, 2-Amino-1,1,3-propenetricarbonitrile, Variamine Blue RT salt, 4,5,6-Triaminopyrimidine sulfate salt, 2-Amino-benzothiazole, Melamine, 3-(3-Pyridylmethylamino)Propionitrile, Silver(I) Sulfadiazine, Acriflavine, 4-Amino-6-mercaptopyrazole[3,4-d]pyrimidine, 2-Aminopurine, Adenine Thiol FAD Fluoroadenine, 4-Amino-6-mercapyopyrazole[3,4-d]pyrimidine, Rhodamine 110, Adenine, 5-Amino-2-mercaptobenzimidazole, Acridine Orange Hydrochloride, Cresyl Violate Acetate, Acriflavine Neutral, Dimidium Bromide, 5,10,15,20-Tetrakis(N-methyl-4-pyridinio)porphyrin Tetra(p-toluenesulfonate), 5,10,15, 20-Tetrakis(4-trimethylaminophenyl)porphyrin Tetra(p-toluenesulfonate), 3,5-Diaminoacridine Hydrochloride, Propidium Iodide (3,8-diamino-5-(3-diethylaminopropyl)-6-phenylphenanthridinium iodidemethiodide), Trans-4-[4-(dimethylamino)styryl]-1-methylpyridinium iodide, and 4-((4-(dimethylamino)phenyl)azo)benzoic acid, succinimidyl ester or derivatives thereof. Preferably, the Raman-active molecular linker is a thiol-group containing compound. In one embodiment, the Raman-active linker molecule is 6-Mercaptopurine.

In various embodiments of the inventive methods, the analyte binding molecule is covalently coupled to the Raman-active molecular linker by amide bond formation. For this coupling a carbodiimide, such as 1-ethyl-3-(3-dimethylaminopropyl)carbodiimide, can be used as a coupling agent.

In various embodiments, the metal substrate surface is made of a noble metal or copper.

The noble metal may be selected from the group consisting of silver and gold.

In some embodiments, the substrate is a nanoparticle. The nanoparticle may be coated with or consisting of a noble metal. The noble metal can, for example, be selected from gold and silver. In one specific embodiment, the nanoparticle is coated with a silver film. In another specific embodiment, the nanoparticle is a citrate-stabilized gold nanoparticle.

In another aspect, the present invention relates to a conjugate for the detection of an analyte using surface-enhanced Raman spectroscopy comprising an analyte binding molecule, a Raman-active linker molecule and a metal substrate, wherein the analyte binding molecule is covalently coupled to the Raman-active linker molecule and the Raman-active linker molecule is covalently attached to the metal substrate. In the conjugate, the analyte binding molecule and/or the Raman-active linker molecule and/or the metal substrate can be as defined above in relation with the invented method.

In still another aspect, the invention is directed to a biosensor for the detection of an analyte using surface-enhanced Raman spectroscopy, comprising one or more conjugates according to the invention. The biosensor may further comprise a substrate, wherein the nanoparticles are adherent to the substrate. In various embodiments, the biosensor is configured for in vivo and/or in vitro use. The analyte may be a protein, peptide, nucleic acid, carbohydrate, lipid, cell, virus, small molecule, or hapten.

In a still further aspect, the invention relates to the use of the biosensor of the invention for the detection of an analyte. The detection may be in vivo or in vitro.

DETAILED DESCRIPTION

Figure 1:
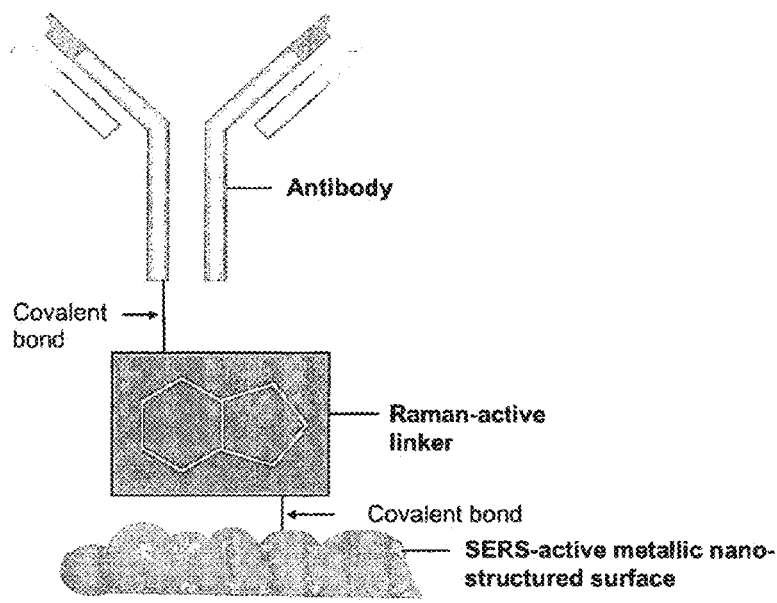
FIG. 1 schematically illustrates the principle of the SERS-based nanoscale sensor.
Figure 1:
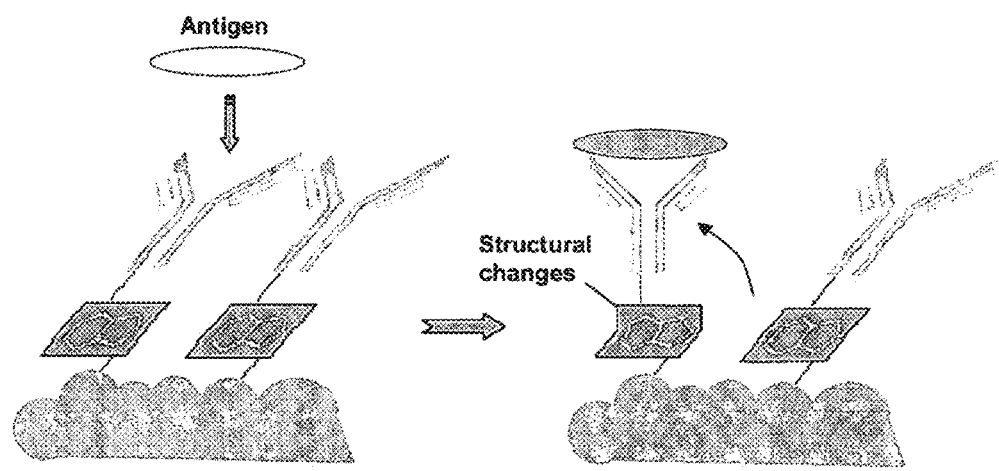
Figure 1:
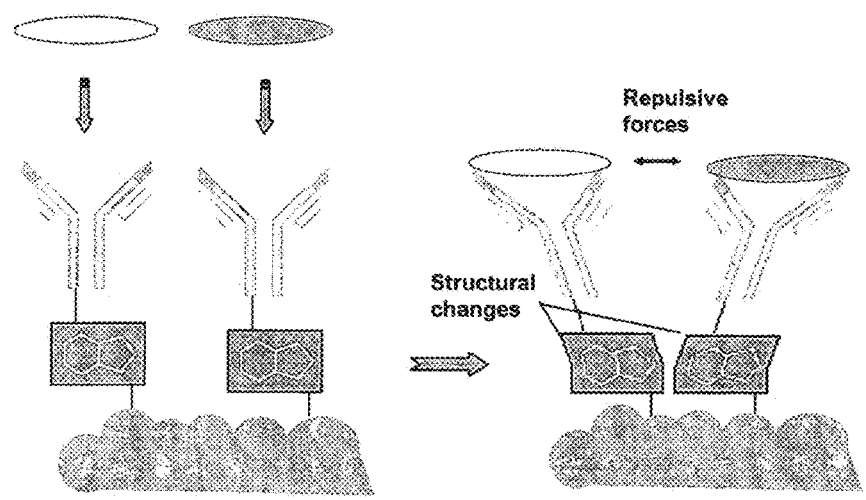

When a molecule interacts with a monochromatic light carrying a photon-energy less than its first electronic transition, two optical processes can occur. In the first, and the dominant, process, a large portion of the incident light is elastically scattered with no photon energy being absorbed; this is known as the Rayleigh scattering. A second, and the relatively weaker, process involves the adsorption of a small amount of the incident photon energy by the molecular system that then undergoes a transition from a one vibrational state to another, followed by a subsequent re-emission of light at a frequency "shifted" from that of the incidence, and such an optical effect is conventionally known as Raman scattering.

One important aspect of the Raman scattering is the correlation between the amount of the frequency shifts and the vibrational modes of the molecules—here, vibrational modes refer to the "manner" in which the molecule vibrates. Since vibrational modes are sensitive to the chemical nature of the molecule, probing molecular vibrations can thus reveal information regarding its chemical geometry. While a plethora of techniques, such as the nuclei magnetic resonance (NMR) and X-ray crystallography, can also provide access to chemical structures, optical measurements of vibrational states via Raman scattering offer a much more convenient approach, owing to the ease of sample preparation (Garman E & Sweet R M, *Methods Mol. Biol.*, 2007, 364, 63-94; Chen J & Brooks C L, *Prot.*, 2007, 67(4), 922-930). For this reason, the Raman spectrum, which is unique to each molecule, was utilized as a "fingerprint" in identifying unknown species, and in a more interesting aspect, Raman scattering is utilized for elucidating conformational changes.

Despite of its high specificity, Raman spectroscopy has limited use due to poor efficiency of Raman scattering. It is estimated that only 1 in every $10^6$-$10^8$ scattered photons is Raman-scattered and this results in a very weak Raman signal.

Surface-enhanced Raman spectroscopy (SERS) was first observed by Fleischman et al in 1974 when remarkably strong Raman signals were obtained for pyridine adsorbed on an electrochemically roughened silver electrode (Fleischman M et al., *Chem. Phys. Lett.*, 1974, 26, 123). Two mechanisms have been widely accepted for bringing about this enhancement in Raman scattering (which can be as high as $10^{14}$ times the unenhanced signal) (Kneipp K et al., *Chem. Rev.*, 1999, 99(10), 2957-2976). They are electromagnetic enhancement and chemical enhancement.

Electromagnetic enhancement accounts for the majority of the enhancement (factor of $10^4$-$10^7$) and arises from the interaction between the analyte that is absorbed or brought in close proximity to the metal surface and the surface plasmon fields excited in the metal by a laser beam (Moskovits M, *J. Raman Spectro.*, 2005, 36(6-7), 485-496). Conduction electrons that reside on the surface of a metal exhibit lateral freedom of motion as they are constricted only by the positive charges on the 'bulk' metal side. When light interacts with these electrons, they oscillate collectively and this oscillation is known as surface plasmon. On a roughened surface, the oscillations are localized and perpendicular to the surface plane, generating a locally amplified electromagnetic fields responsible for the SERS effect.

The localized surface plasmons (LSP) have a resonant frequency at which the absorption and scattering of light occurs most efficiently. This frequency is dependent upon the metal and the nature of the surface (size, roughness, shape, interparticle spacing and dielectric environment) (Kelly K L et al., *J. Phys. Chem. B*, 2003, 107(3), 668-677). This is of importance in the fabrication of SERS substrates as one may want to manipulate the resonant frequency to be close to the excitation frequency used to ensure maximal enhancements (Haynes C L & Van Duyne R P, *J. Phys. Chem. B*, 2003, 107(30), 7426-7433).

Chemical enhancement is argued to contribute only an order of $10$-$10^2$ order to the overall enhancement (Liang E J & Kiefer W, *J. Raman Spectro.*, 1996, 27(12), 879-885). It involves electron coupling between the analyte and metal surface that changes the polarizability of the molecule and forming a surface species that act as resonant intermediates in the Raman scattering. A charge transfer mechanism between the analyte and metal has also been proposed.

A SERS substrate normally refers to a well-engineered metallic nanostructure on which the analytes are absorbed for SERS acquisitions. There are three classes of SERS substrates: roughened metal surfaces, colloidal metal nanoparticles, and planar metallic structures such as arrays of metal nanoparticles supported on a planar substrate like glass (Vo-Dinh T, *Trac-Trends. Anal. Chem.*, 1998, 17(8-9), 557-582; Baker G A & Moore D S, *Anal. Bioanal. Chem.*, 2005, 382(8), 1751-1770). As mentioned earlier, the LSP responsible for SERS enhancement is highly dependent upon the surface characteristics of the SERS substrate, making SERS a surface-sensitive technique.

As proteins are weak Raman scatterers their binding to a substrate cannot be easily detected using SERS. However, the inventors of the present invention have found that proteins can be detected using a SERS-based nanoscale stress sensor. In this setup, an analyte binding molecule, such as an antibody, is coupled to a substrate immobilized SERS active substance. By stressing, e.g. stretching and compressing the bonds of the SERS active substance to the substrate and/or antibody as a result of the analyte binding event detectable shifts in the SERS spectrum are induced. Surprisingly, this allows highly sensitive and specific detection of analyte binding.

Thus, in a first aspect, the present invention is directed to a method for detecting one or more analytes using surface enhanced Raman spectroscopy (SERS), comprising
contacting the one or more analytes with at least one analyte binding molecule attached to a metal substrate surface that enhances Raman scattering via a Raman-active molecular linker; and detecting a surface enhanced Raman signal from said compound.

The terms "at least one" or "one or more" as used interchangeably herein in connection with molecules relates to 1, 2, 3 or more, for example at least 1, 2, 3, 4, 5, 6, 7, 8, 9, 10, 12, 14, 15, 20, 25 or a plurality of molecules. In this connection, the term "plurality" means more than two, preferably 3-100.

The term "analyte binding molecule" as used herein refers to any molecule capable of binding to an analyte of choice so as to form a complex consisting of the analyte binding molecule and the analyte. Preferably, this binding is specific so that a specific complex between analyte and analyte binding molecule is formed.

"Specifically binding" and "specific binding" as used herein mean that the analyte binding molecule binds to the target analyte based on recognition of a binding region or epitope on the target molecule. The analyte binding molecule preferably recognizes and binds to the target molecule with a higher binding affinity than it binds to other compounds in the sample. In various embodiments of the invention, "specifically binding" may mean that an antibody or other biological molecule, binds to a target molecule with at least about a $10^6$-fold greater affinity, preferably at least about a $10^7$-fold greater affinity, more preferably at least about a $10^8$-fold greater affinity, and most preferably at least about a $10^9$-fold greater affinity than it binds molecules unrelated to the target molecule. Typically, specific binding refers to affinities in the range of about $10^6$-fold to about $10^9$-fold greater than non-specific binding. In some embodiments, specific binding may be characterized by affinities greater than $10^9$-fold over non-specific binding. The binding affinity may be determined by any suitable method. Such methods are known in the art and include, without limitation, surface plasmon resonance and isothermal titration calorimetry. In a specific embodiment, the analyte binding molecule uniquely recognizes and binds to the target analyte.

The analyte binding molecule may be a proteinaceous molecule, such as an antibody, for example a monoclonal or polyclonal antibody, which immunologically binds to the target analyte at a specific determinant or epitope. The term "antibody" is used in the broadest sense and specifically covers monoclonal antibodies as well as antibody variants or fragments (e.g., Fab, F(ab')$_2$, scFv, Fv diabodies and linear antibodies), so long as they exhibit the desired binding activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. The monoclonal antibodies can include "chimeric" antibodies and humanized antibodies. A "chimeric" antibody is a molecule in which different portions are derived from different animal species, such as those having a variable region derived from a murine mAb and a human immunoglobulin constant region.

Monoclonal antibodies may be obtained by any technique that provides for the production of antibody molecules by continuous cell lines in culture. These include, but are not limited to the hybridoma technique of Koehler and Milstein (U.S. Pat. No. 4,376,110), the human B-cell hybridoma technique, and the EBV-hybridoma technique. Such antibodies may be of any immunoglobulin class including IgG, IgM, IgE, IgA, IgD and any subclass thereof. The hybridoma producing the mAb may be cultivated in vitro or in vivo. Production of high titres of mAbs in vivo makes this a very effective method of production.

"Polyclonal antibodies" are heterogeneous populations of antibody molecules derived from the sera of animals immunized with an antigen, or an antigenic functional derivative thereof. For the production of polyclonal antibodies, host animals such as rabbits, mice and goats, may be immunized by injection with an antigen or hapten-carrier conjugate optionally supplemented with adjuvants.

Alternatively, techniques described for the production of single chain antibodies (U.S. Pat. No. 4,946,778) can be used to produce suitable single chain antibodies. Single chain antibodies are typically formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments that can be produced by pepsin digestion of the antibody molecule and the Fab fragments that can be generated by reducing the disulfide bridges of the F(ab')$_2$ fragments. Alternatively, Fab expression libraries may be constructed to allow rapid and easy identification of monoclonal Fab fragments with the desired specificity.

The analyte binding molecule may also be any other proteinaceous scaffold that has been adapted or mutated to bind a given ligand with sufficient binding affinity.

Examples of useful scaffolds include those scaffolds described in US patent application 2005/0089932 or U.S. Pat. No. 6,682,736. Another example of suitable scaffolds are members of the lipocalin protein family as described in the international patent applications WO 99/16873, WO 00/75308, WO 03/029471, WO 03/029462, WO 03/029463, WO 2005/019254, WO 2005/019255 or WO 2005/019256, for instance.

In accordance with the above, scaffolds besides members of the lipocalin family include, but are not limited to, a EGF-like domain, a Kringle-domain, a fibronectin type I domain, a fibronectin type II domain, a fibronectin type III domain, a PAN domain, a Gla domain, a SRCR domain, a Kunitz/Bovine pancreatic trypsin inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, Kappabodies, Minibodies, Janusins, a nanobody, a adnectin, a tetranectin, a microbody, an affilin, an affibody or an ankyrin, a crystallin, a knottin, ubiquitin, a zinc-finger protein, an ankyrin or ankyrin repeat protein or a leucine-rich repeat protein, an avimer; as well as multivalent avimer proteins evolved by exon shuffling of a family of human receptor domains.

As mentioned above, in certain embodiments of the invention the analyte binding molecule may be a mutein of the member of the lipocalin protein family. In some of these embodiments, the open end of the β-barrel structure of the lipocalin fold (which encompasses the natural ligand binding site of the lipocalin family) is used to form the target analyte binding site. Members of the lipocalin family of proteins include, but are not limited to the bilin binding protein of *Pieris brassicae* (SWISS-PROT Data Bank Accession Number P09464), human tear lipocalin (SWISS-PROT Data Bank Accession Number M90424), human apolipoprotein D (SWISS-PROT Data Bank Accession Number P05090), the retinol binding protein (RBP) (for example of human or porcine origin, SWISS-PROT Data Bank Accession Number of the human RBP: P02753, SWISS-PROT Data Bank Accession Number of the porcine RBP P27485), human neutrophil gelatinase-associated lipocalin (hNGAL, SWISS-PROT Data Bank Accession Number P80188), rat $\alpha_2$-microglobulin-related protein (A2m, (SWISS-PROT Data Bank Accession Number P31052), and mouse 24p3/uterocalin (24p3, (SWISS-PROT Data Bank Accession Number P11672), Von Ebners gland protein 2 of *Rattus norvegicus* (VEG protein 2; SWISS-PROT Data Bank Accession Number P41244), Von Ebners gland protein 2 of *Sus scrofra* (pig) (LCN1; SWISS-PROT Data Bank Accession Number P53715), the Major allergen Can f1 precursor of dog (ALL 1, SWISS-PROT Data Bank Accession Number O18873), and insecticyanin A or insecticyanin B of the tobacco hawkmoth *Manducta sexta* (SWISS-PROT Data Bank Accession Number P00305 and Q00630, respectively).

The analyte binding molecule may also be a binding protein, receptor or extracellular domain (ECD) thereof capable of forming a binding complex with a ligand, typically a polypeptide or glycopeptide ligand.

Those skilled in the art will recognized that the non-limiting examples given above describing various forms of antibodies as analyte binding molecules can also be extended to other proteinaceous receptors such as recombinant, chimeric, hybrid, truncated etc., forms of non-antibody receptors.

The analyte-binding molecule can also be a non-proteinaceous receptor, such as for example a nucleic acid based molecule, such as an Aptamer or Spiegelmer (Aptamer made of L-ribonucleotides).

In case the analyte binding molecule is a proteinaceous molecule it can be covalently coupled to the Raman-active molecular linker by amide bond formation. This covalent coupling can be achieved by carbodiimide coupling, for example using 1-ethyl-3-(3-dimethylaminopropyl) carbodiimide as a coupling agent. The coupling can be via the N- or C-terminus or via one or more side chains of the amino acids of the protein. Side chains that can be used for this covalent coupling include, but are not limited to lysine, histidine, cysteine, tyrosine, serine, threonine, aspartic acid and glutamic acid side chains.

The term "linker" or "linker molecule" refers to a Raman-active molecule that links the analyte binding molecule to the substrate surface and facilitates detection of an analyte specifically bound by the analyte binding molecule via a change in the SERS signal. The Raman-active molecule interacts with the substrate surface and thus provides for a SERS signal. In principle any molecule that can generate a SERS signal upon interaction with a Raman-active surface and that produces a change in the SERS signal as a result of molecular stresses caused by analyte binding to the analyte binding protein can be used. The Raman-active molecular linker can be selected from a variety of known Raman-active compounds that include, but are not limited to 6-Mercaptopurine, 8-Aza-adenine, N-Benzoyladenine, 2-Mercaptobenzimidazole, 4-Amino-pyrazole[3,4-d]pyrimidine, Zeatin, Methylene Blue, 9-Amino-acridine, Ethidium Bromide, Bismarck Brown Y, N-Benzyl-aminopurine, Thionin acetate, 3,6-Diaminoacridine, 6-Cyanopurine, 4-Amino-5-imidazole-carboxamidehydrochloride, 1,3-Diiminoisoindoline, Rhodamine 6G, Crystal Violet, Basic Fuchsin, Aniline Blue Diammonium salt, N-[(3-(Anilinomethylene)-2-chloro-1-cyclohexen-1-yl)methylene]anilinemonohydrochloride, O-(7-Azabenzotriazol-1-yl)-N,N,N',N'-tetramethyluroniumhexafluorophosphate, 9-Aminofluorene hydrochloride, Basic Blue, 1,8-Diamino-4,5-dihydroxyanthraquinone, Proflavine hemisulfate salt hydrate, 2-Amino-1,1,3-propenetricarbonitrile, Variamine Blue RT salt, 4,5,6-Triaminopyrimidine sulfate salt, 2-Amino-benzothiazole, Melamine, 3-(3-Pyridylmethylamino)Propionitrile, Silver(I) Sulfadiazine, Acriflavine, 4-Amino-6-mercaptopyrazole[3,4-d]pyrimidine, 2-Aminopurine, Adenine Thiol FAD Fluoroadenine, 4-Amino-6-mercapyopyrazole[3,4-d]pyrimidine, Rhodamine 110, Adenine, 5-Amino-2-mercaptobenzimidazole, Acridine Orange Hydrochloride, Cresyl Violate Acetate, Acriflavine Neutral, Dimidium Bromide, 5,10,15,20-Tetrakis(N-methyl-4-pyridinio)porphyrin Tetra(p-toluenesulfonate), 5,10,15,20-Tetrakis(4-trimethylaminophenyllporphyrin Tetra(p-toluenesulfonate), 3,5-Diaminoacridine Hydrochloride, Propidium Iodide (3,8-diamino-5-(3-diethylaminopropyl)-6-phenylphenanthridinium iodidemethiodide), Trans-4-[4-(dimethylamino)styryl]-1-methylpyridinium iodide, and 4-((4-(dimethylamino)phenyl)azo)benzoic acid, succinimidyl ester and derivatives thereof. "Derivatives" refers to modified compounds that are structurally closely related to the parent compound. Preferred derivatives are compounds that have been modified such that they comprise a thiol (SH) group. The thiol group allows covalent coupling of the linker molecule to a metal surface. The inventive methods thus comprise embodiments, where the Raman-active molecular linker is attached to the substrate surface via covalent interactions.

The terms "analyte", "target compound", "target molecule" or "target" as interchangeably used herein, refer to any substance that can be detected in an assay by binding to a binding molecule, and which, in one embodiment, may be present in a sample. Therefore, the analyte can be, without limitation, any substance for which there exists a naturally occurring antibody or for which an antibody can be prepared. The analyte may, for example, be an antigen, a protein, a polypeptide, a nucleic acid, a hapten, a carbohydrate, a lipid, a cell or any other of a wide variety of biological or non-biological molecules, complexes or combinations thereof. Generally, the analyte will be a protein, peptide, carbohydrate or lipid derived from a biological source such as bacterial, fungal, viral, plant or animal samples. Additionally, however, the target may also be a small organic compound such as a drug, drug-metabolite, dye or other small molecule present in the sample.

The term "sample", as used herein, refers to an aliquot of material, frequently biological matrices, an aqueous solution or an aqueous suspension derived from biological material. Samples to be assayed for the presence of an analyte by the methods of the present invention include, for example, cells, tissues, homogenates, lysates, extracts, and purified or partially purified proteins and other biological molecules and mixtures thereof.

Non-limiting examples of samples typically used in the methods of the invention include human and animal body fluids such as whole blood, serum, plasma, cerebrospinal fluid, sputum, bronchial washing, bronchial aspirates, urine, semen, lymph fluids and various external secretions of the respiratory, intestinal and genitourinary tracts, tears, saliva, milk, white blood cells, myelomas and the like; biological fluids such as cell culture supernatants; tissue specimens which may or may not be fixed; and cell specimens which may or may not be fixed. The samples used in the methods of the present invention will vary based on the assay format and the nature of the tissues, cells, extracts or other materials, especially biological materials, to be assayed. Methods for preparing protein extracts from cells or samples are well known in the art and can be readily adapted in order to obtain a sample that is compatible with the methods of the invention. Detection in a body fluid can also be in vivo, i.e. without first collecting a sample.

"Peptide" generally refers to a short chain of amino acids linked by peptide bonds. Typically peptides comprise amino acid chains of about 2-100, more typically about 4-50, and most commonly about 6-20 amino acids. "Polypeptide" generally refers to individual straight or branched chain sequences of amino acids that are typically longer than peptides. "Polypeptides" usually comprise at least about 20 to 1000 amino acids in length, more typically at least about 100 to 600 amino acids, and frequently at least about 200 to about 500 amino acids. Included are homo-polymers of one specific amino acid, such as for example, poly-lysine. "Proteins" include single polypeptides as well as complexes of multiple polypeptide chains, which may be the same or different.

Multiple chains in a protein may be characterized by secondary, tertiary and quaternary structure as well as the primary amino acid sequence structure, may be held together, for example, by disulfide bonds, and may include post-synthetic modifications such as, without limitation, glycosylation, phosphorylation, truncations or other processing.

Antibodies such as IgG proteins, for example, are typically comprised of four polypeptide chains (i.e., two heavy and two light chains) that are held together by disulfide bonds. Furthermore, proteins may include additional components such associated metals (e.g., iron, copper and sulfur), or other moieties. The definitions of peptides, polypeptides and proteins includes, without limitation, biologically active and inactive forms; denatured and native forms; as well as variant, modified, truncated, hybrid, and chimeric forms, thereof.

The terms "contacting" or "incubating" as used interchangeably herein refer generally to providing access of one component, reagent, analyte or sample to another. For example, contacting can involve mixing a solution comprising an analyte binding protein or conjugate thereof with a sample. The solution comprising one component, reagent, analyte or sample may also comprise another component or reagent, such as dimethyl sulfoxide (DMSO) or a detergent, which facilitates mixing, interaction, uptake, or other physical or chemical phenomenon advantageous to the contact between components, reagents, analytes and/or samples.

The term "detecting" as used herein refers to a method of verifying the presence of a given molecule. The technique used to accomplish this is surface enhanced Raman spectroscopy (SERS). The detection may also be quantitative, i.e. include correlating the detected signal with the amount of analyte. The detection includes in vitro as well as in vivo detection.

The term "hapten" as used herein, refers to a small proteinaceous or non-protein antigenic determinant which is capable of being recognized by an antibody. Typically, haptens do not elicit antibody formation in an animal unless part of a larger species. For example, small peptide haptens are frequently coupled to a carrier protein such as keyhole limpet hemocyanin in order to generate an anti-hapten antibody response.

"Antigens" are macromolecules capable of generating an antibody response in an animal and being recognized by the resulting antibody. Both antigens and haptens comprise at least one antigenic determinant or "epitope", which is the region of the antigen or hapten which binds to the antibody. Typically, the epitope on a hapten is the entire molecule.

The method of the invention can also be a multiplex method for detecting more than one analyte, i.e. two or more different analytes. This usually requires the use of more than one analyte binding molecule in the contacting step so that each analyte is bound by a specific analyte binding molecule. The signal obtained from a multitude of different analyte binding molecule:analyte complexes can be resolved by using different Raman-active linker molecules that produce distinct SERS signals.

The metal substrate surface may be made of a noble metal or copper. "Noble metal", as used herein, relates to a metal selected from the group consisting of ruthenium, rhodium, silver, palladium, osmium, iridium, platinum, and gold, preferably silver and gold.

The substrate may be a nanoparticle, for example a nanoparticle coated with or consisting of a noble metal, as defined above, or copper. The nanoparticle can be coated with a silver film or can be a citrate-stabilized gold nanoparticle. "Nanoparticle" as used herein relates to a particle sized between 1 and 100 nanometers.

The invention also encompasses conjugates for the detection of an analyte using surface-enhanced Raman spectroscopy, wherein these conjugates comprising an analyte binding molecule, a Raman-active linker molecule and a metal substrate, all defined as above. The term "conjugate" as used herein refers to two or more molecules which have been linked together. The linkage to each other may be covalent or non-covalent, but preferably is covalent. In one embodiment of such a conjugate, the analyte binding molecule is covalently coupled to the Raman-active linker molecule and the Raman-active linker molecule is covalently attached to the metal substrate.

These conjugates can be part of a kit for the detection of a given analyte or the conjugate components can, together with coupling agents, form part of a kit, requiring that before use, the conjugate is formed.

The invention also relates to a biosensor for the detection of an analyte using surface-enhanced Raman spectroscopy, comprising one or more of the above conjugates, in particular nanoparticle conjugates. The biosensor may further comprise a substrate with the nanoparticles being attached to or adherent to the substrate. The biosensor can be configured for in vivo and/or in vitro use. The use of such a biosensor is a further aspect of the present invention. This use can be in vivo or in vitro and may comprise contacting the biosensor with the analyte containing medium, for example a sample or body fluid, and detecting the SERS signal from the sensor. In a preferred embodiment, the biosensor is configured for a multiplex method that allows the detection of more than one analyte.

One embodiment of the invention is illustrated in FIG. 1a. In this particular embodiment, an antibody chosen to target a specific analyte of interest, which can be as defined above, is anchored onto a SERS-active metallic nanostructured surface via a Raman-active molecular linker. The linker schematically displayed in the Figure merely serves as an example and is not intended to be limiting. Linker molecule containing no aromatic ring or a plurality of aromatic rings in some suitable arrangement can also be used. To ensure a firm attachment of the antibody to the nanostructures, the antibody is covalently connected to one end of the linker molecule through an appropriate chemical reaction, e.g. through an amide-bond formation by 1-ethyl-3-(3-dimethylaminopropyl) carbodiimide (EDC) zero-length coupler, while the other end of the linker molecule is covalently attached to the metallic nanostructure through a thiol moiety, thereby anchoring the antibody to the nanostructure.

While the different components can be replaced by other suitable compounds, such molecular arrangement is crucial for the operation of the current sensor system.

The inventors of the present invention have observed and shown that binding of an antigen molecule to its antibody could induce structural changes in both members, i.e. the antibody and the linker molecule, due to binding-related stress. Without wishing to be bound to any particular theory, it is hypothesized that a multitude of factors could give rise to such a binding-related stress. For instance, electrostatic repulsion as well as steric interactions between two dipole like molecules can give rise to stress. It has also been suggested that although electrostatic and steric repulsion may play a role, configurational entropy may supersede these forces and lead to molecular re-orientation/configuration which subsequently brings about stress. In addition, hydration forces between neighboring bound molecules may also result in stress. The inventors have now unexpectedly found that these forces can be exploited for the detection of antigen/antibody binding events. A more elaborated picture of this inventive concept is schematically illustrated in FIGS. 1b and 1c.

In the example given in FIG. 1b, the antibody/linker construct is initially oriented at a specific angle. Upon binding of an antigen to the antibody, repulsion forces, which could be steric, electrostatic, hydration, entropic in nature, are induced, bringing about a re-orientation of the antibody/linker construct. This re-orientation subsequently produces bending stress and results in changes in the internal structure of the linker molecule. Due to the proximity of the linker molecule to the SERS-active surface, such a re-orientation induced structural changes within the molecule becomes detectable via SERS spectrometric analysis. In another example depicted in FIG. 1c, the antibody/linker construct is initially oriented normally with respect to the SERS-active surface. Upon binding to antigens, repulsion forces between neighboring antigen molecules result in a re-orientation of the antibody/linker constructs, and in turn bending stresses within the linker's structure. As in the first example, such stress can also be indirectly measured through SERS spectrometric analysis.

With the current embodiment, it is apparent that no washing step may be required for the detection of the binding events since the unbound antigens or contaminants within the sample medium are not within the reach of the plasmon near-field on the SERS-active surface, and thus their Raman signals are not amplified and therefore negligible as compared to the linker signals. Another advantage offered by the current design is the uniqueness of the Raman spectrum of the linker, which allows for discrimination against Raman background, thereby improving overall system's sensitivity.

Figure 2:
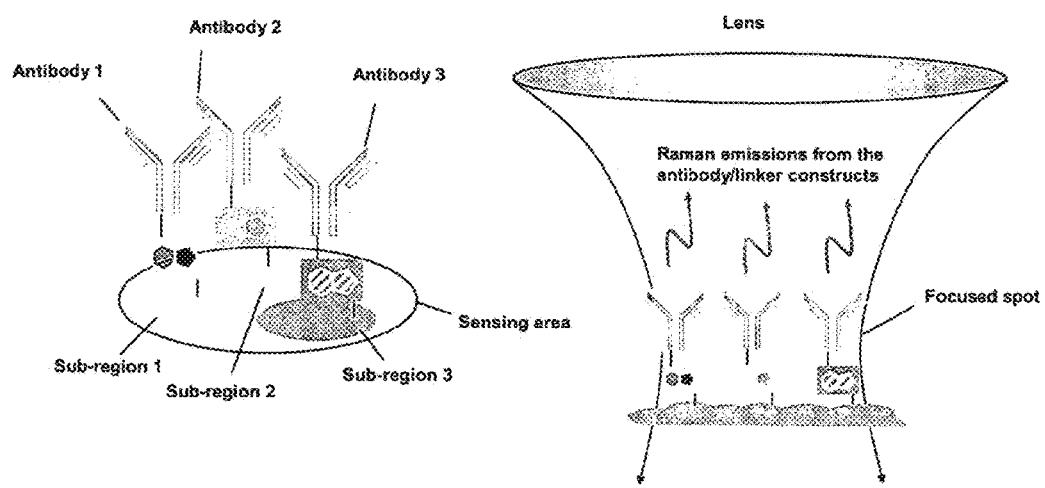
FIG. 2 schematically illustrates the principle of a multiplexed SERS-based nanoscale sensor.

Another embodiment of the current invention is illustrated in FIG. 2a. This embodiment concerns a highly-multiplexed SERS-based nanoscale stress sensor for protein detection. The inventors found out that this sensor can be much more miniaturized than previous fluorescent detection methods, as it is devoid of significant spectral overlaps. The narrow peak-width in the SERS spectra means that signal cross-talk can be minimized, thereby allowing simultaneous measurement of multiple binding events to be performed within a single laser spot. Thus, the current design is expandable to a highly-multiplexed sensing platform.

In this particular embodiment, the sensing area is subdivided into several regions, each of which bears a specific antibody/linker construct. As an example, three different antibody/linker constructs are shown in FIG. 2a. It should be noted that each of the three antibody/linker constructs is comprised of a different antibody and linker molecule so that up to 3 antigens can be targeted simultaneously per sensing area. In one aspect of this particular embodiment, it is not a requirement that each sub-region within the sensing area be comparable in size with the laser spot. In fact, each sub-region can be smaller than the laser spot, so that more than one binding events can be simultaneously probed within a single laser spot (see drawing on the right of FIG. 2a). This is made possible by the fact that SERS spectra of different linker molecules are generally not significantly overlapped and thus can be computationally separated. In fact, more than three binding events can be probed simultaneously by one single laser spot, so long as the SERS spectra of the linker are separable. This embodiment thus offers the possibility of a highly-multiplexed protein sensing system.

Other embodiments are within the following non-limiting examples.

EXAMPLES

Example 1

Chemicals 6-mercaptopurine (6-MP) monohydrate and 1-ethyl-3-(3-dimethylaminopropyl) carbodiimide (EDC) were obtained from Sigma Aldrich. Glycine and phosphate buffer saline (PBS, pH7.4) were obtained from Invitrogen and $1^{st}$ BASE respectively. Purified mouse anti-human p53 (0.5 mg/ml) and recombinant human p53 (10 µg in 100 µl) were procured from BD Biosciences Pharmingen. The Gold SERS substrates used in this experiment were fabricated by e-beam lithography.

Example 2

Coupling of 6-MP to the SERS Substrate 15.2 mg of 6-mercaptopurine (6-MP) were dissolved in PBS to make an approximately 10 mM solution. A clean Au IME substrate was immersed in this solution for an hour before it was rinsed with demonized water and left to dry. A Raman spectrum was taken before and after treatment with 6-MP.

Example 3

Immobilization of anti-human p53 onto 6-MP-coated SERS substrates

4 µl of anti-human p53 was added to 0.5 ml PBS. 650 µM of EDC solution was prepared by dissolving 2.4 mg EDC in 20 ml PBS. 5 µl of the EDC solution was added to the anti-human p53 in PBS. The 6-MP coated SERS substrate was immersed in this solution for 2 hours at room temperature after which, it was washed thoroughly with PBS and briefly dried.

Example 4

SERS Measurements

2 µl of p53 was added to 20 µl of PBS. This solution was added to the substrate and incubated for 30 minutes at room temperature. A SERS measurement was then taken. Afterwards, the substrate was rinsed thoroughly with deionized water and a SERS measurement was taken in PBS.

Figure 3:
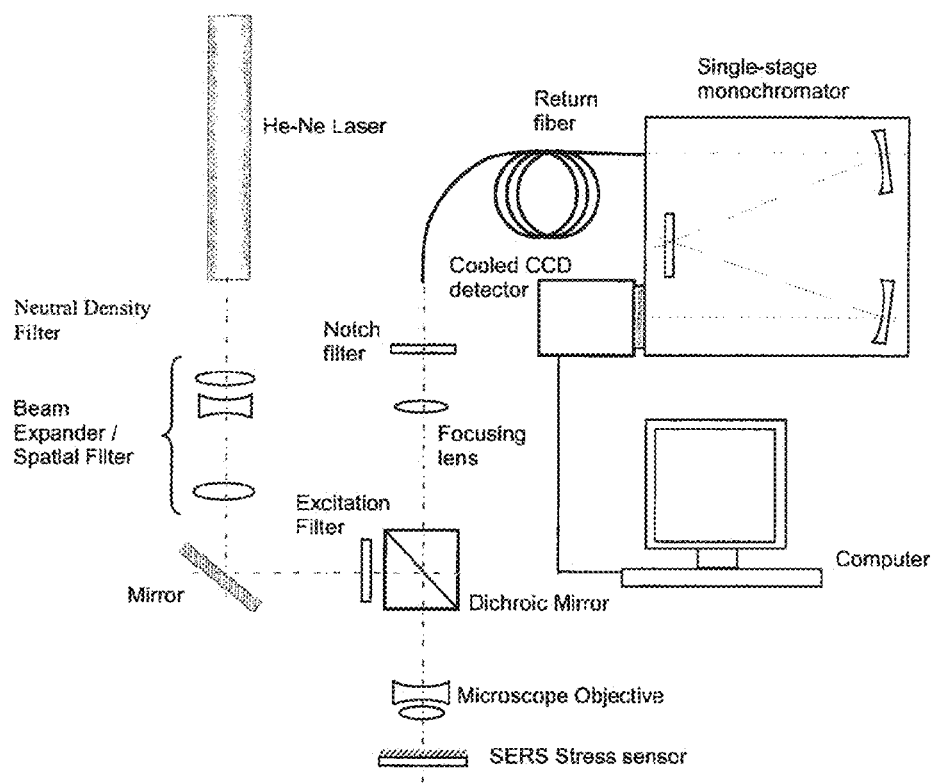
FIG. 3 is a schematic drawing of the experimental setup for SERS measurements.

A scheme of the experimental setup is shown in FIG. 3. Briefly, a 10 mW He—Ne 632.8 nm laser was attenuated to about 5 mW using a neutral density filter (Edmund Inc.). A set of lenses which acts as both a beam expander and spatial filter was used to produce a 7 mm (Ø) beam of uniform profile. The so obtained beam was focused onto the sensing area of the SERS stress sensor via a dichroic mirror and through an Olympus 40×, 0.90 NA microscope objective. The substrate was affixed onto a glass slide via double-sided tape. 20 µl of a p53 solution was dropped onto the substrate and covered with a cover slip before placing onto the microscope stage of the Raman system. The laser power at the sample was measured to be 6 mW. The acquisition time used in the experiment was 10 s with all Raman spectra collected from 200-2000 cm$^{-1}$. The Raman signals generated at the sensor were collected by the same objective and focused into a 400 µm optical fiber (Ocean Optics, Inc.) which delivered the signals to a single-stage monochromator (DoongWo, Inc.). The grating used in this study was 600 g/mm, and the CCD detector (ANDOR Inc.) operating temperature was set to −60° C. An ANDOR software was used to acquire the Raman spectra as well as to control the spectrometer.

The raw SERS spectra were processed using the Wire 3.0 software provided by manufacturer of the Raman system. A straight line baseline subtraction was first performed to remove any background fluorescence. Curve fitting of prominent peaks was carried out using 50% Gaussian curves to locate the centre peak position and determine the peak width and peak intensity.

Figure 4:
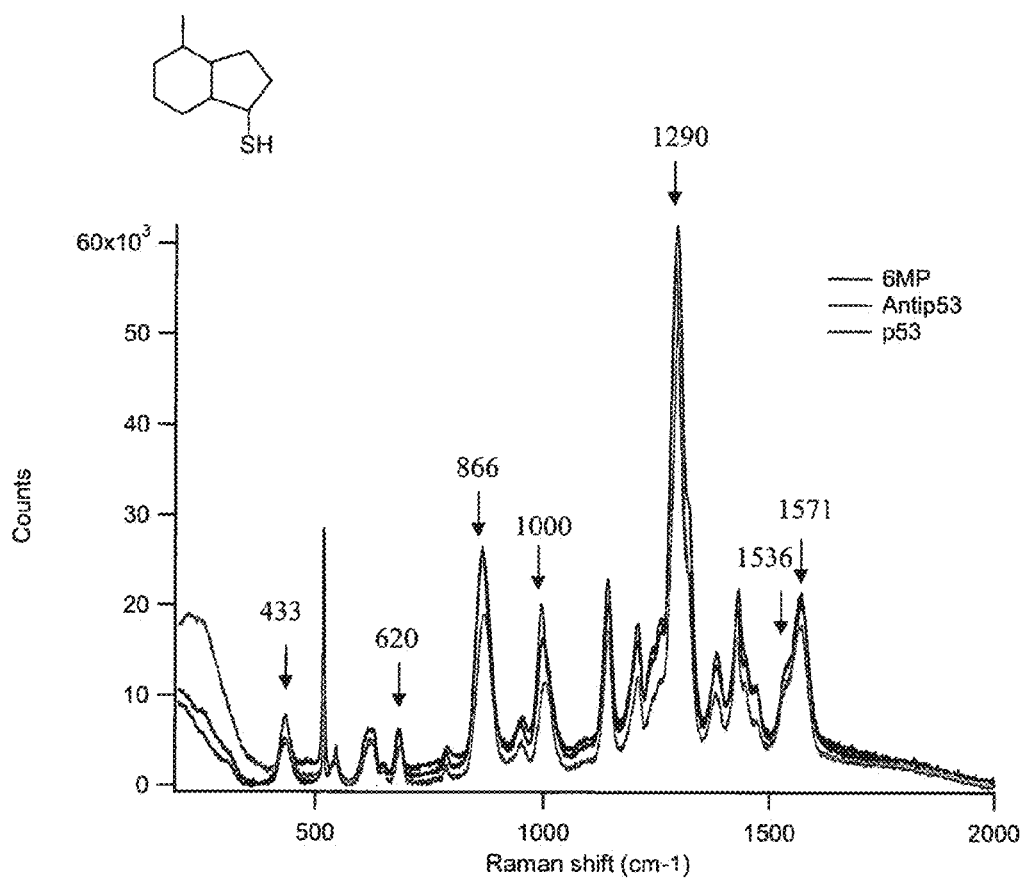
FIG. 4 shows SERS spectra derived from a sensor according to the invention using 6-mercaptopurine (6-MP) as a Raman-active linker molecule.

Exemplary SERS spectra derived from the 6-MP stress sensor are shown in FIG. 4. It is obvious that the shapes of the three spectra are generally similar and no new peaks are formed due to antibody coupling to the sensor surface and analyte binding. This is because the proteins are weak Raman scatterers and the enhancement effect in SERS decays rapidly as the separation of the analyte and metallic nanostructures increases. Therefore, a contribution from the anti-p53 antibody and the p53 antigen would not be significant alongside the spectrum of 6-MP.

The SERS peak positions before and after the addition of p53 were curve fitted and the center wavenumbers tabulated in Table 1. The peaks at ~433, ~620, ~866, ~1000 and 1290 cm$^-$ show significant positive shifts upon addition of p53 with ~866 and ~1000 cm$^{-1}$ peaks displaying the greatest percent shift of ~0.45%. Significant negative shifts were also observed for ~1536 and ~1571 cm$^{-1}$ peaks. To understand the spectral shifts, it is necessary to revisit the theory of Raman scattering as well as understand the interaction of light with a molecule as determined by its energy levels. There are two types of energy levels: electronic energy level, associated with movement of electrons and vibrational, rotational or translational energy level, associated with movement of atoms in the molecule. Each electronic level will have its subset of vibrational levels. Raman scattering, unlike optical absorption, does not require that the incident photon energy coincide with energy transition to the next electronic level. Instead, an incident photon is usually much lower in energy and excites the molecule to an intermediate virtual state from a ground vibrational level. The virtual state is unsteady and a photon is simultaneously scattered with the molecule returning to a lower vibrational level other than ground. The energy of the scattered photon corresponds to the difference between the energy of the incident photon and the energy transition between the vibrational levels (Raman shift). Therefore, vibrations in molecules are the origin of the Raman Effect. These vibrations are constrained in a molecule by the chemical bonds between the constituent atoms. The observed peak shifts in the current experiment are thus suggestive of compression or stretching of certain bonds within 6-MP upon binding of the p53 to the immobilized anti-p53 antibody. When a bond is compressed or constrained, the vibration frequency increases, resulting in a higher Raman shift. The reverse is true for stretched or un-constrained bond. From Table 1, it can be observed that the bonds that have an upshift are bonds that bind 6-MP to the gold substrate (S—Au) and that to anti-p53 (N9). Also, the peaks with the most upshift (~865 and '1000 cm$^{-1}$) correspond to S—Au vibration. This can be explained by being 6-MP's main linkage to the substrate, and thus the S—Au bond experiences the greatest compression upon p53 binding.

TABLE 1

Band assignment of shifted peaks

| Shift | Peak (cm$^{-1}$) | Assignment |
|---|---|---|
| Upshift | 433.54 | (v)S—C6, (br)pyrim |
|  | 620.42 | (δ)C8—H(op), (δ)N9—H |
|  | 865.99 | (br)pyrim, (δ)S—Au |
|  | 1000.04 | (δ)S—Au |
|  | 1290 | (v)N1—C2—N3 |
| Downshift | 1536.02 | (v)N7—C8, (δ)C8—H, (δ)N9—H |
|  | 1571.92 | (v)C2—N1, (v)C6—C5—C4, (δ)N9—H |

Abbreviations: v: stretching vibration; br: ring breathing vibration; δ: deformation vibration; op: out of plane; pyrim: pyrimidine.

Figure 5:
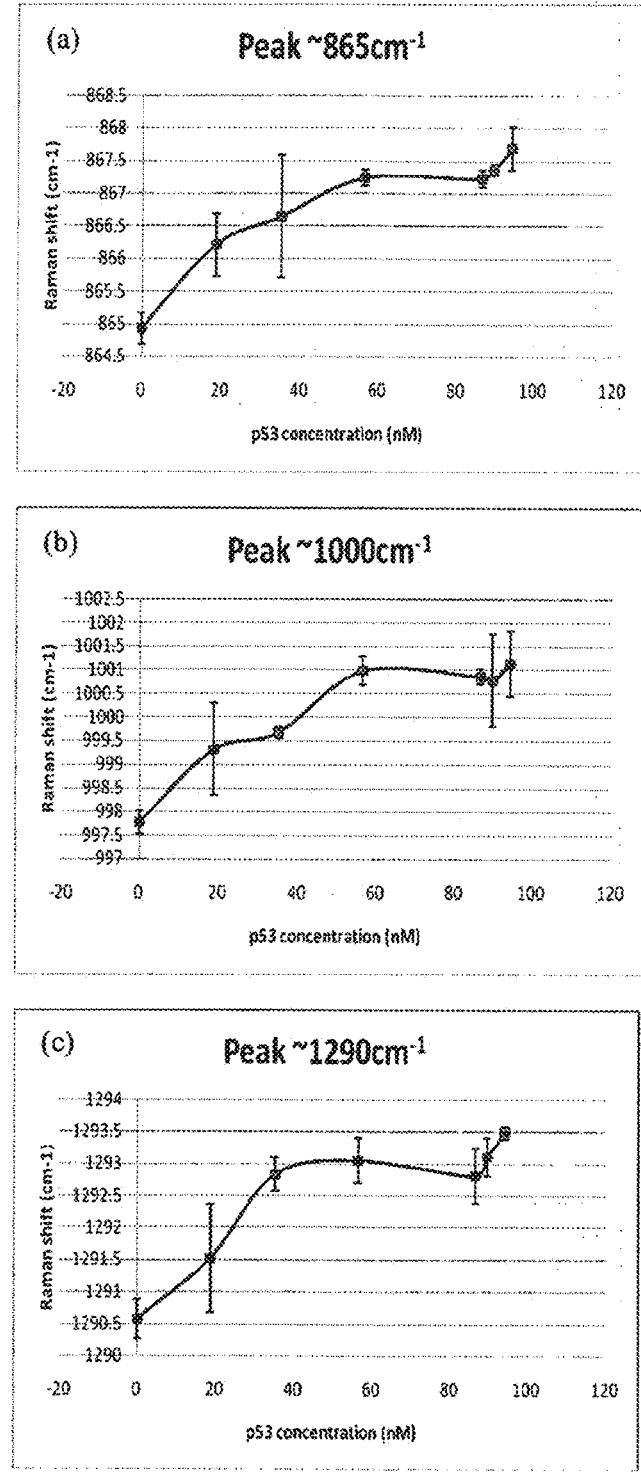
FIG. 5 shows response curves of the SERS-based sensor versus antigen concentrations.

Response curves for the current sensor were constructed by plotting the peak shifts at 865, 1000 and 1290 cm$^{-1}$ against the p53 concentrations. The curves are shown in FIG. 5. These three peaks were arbitrarily chosen to monitor the p53/anti-p53 binding event simply because of having the most significant upshifts and a relatively large intensity. It should be understood that other binding-sensitive peaks can also be used. From FIG. 5, it can be seen that the current sensor is responsive to p53 antigen even at concentrations as low as 10 nM.

Figure 6:
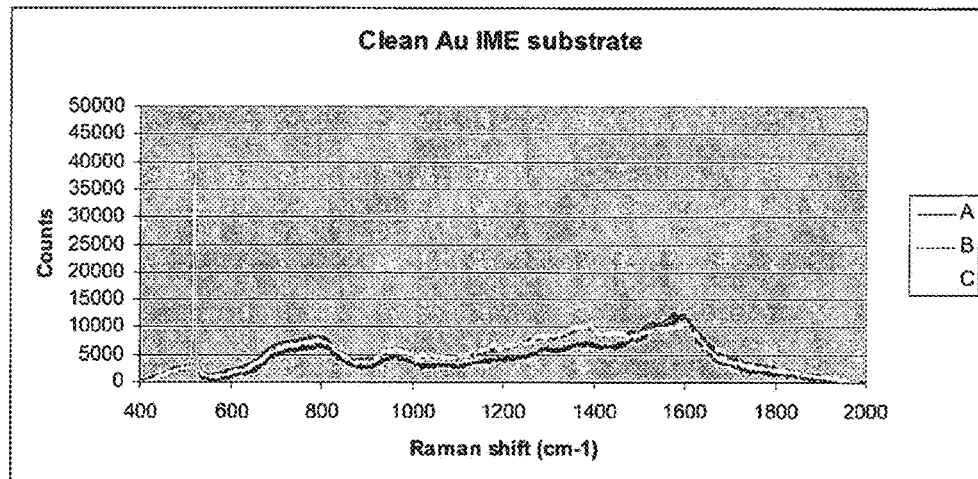
FIG. 6 shows spectra of clean substrate taken at 100% power, 10s acquisition and 1 accumulation. The three curves represent the spectra of three measurements A, B and C.
Figure 7:
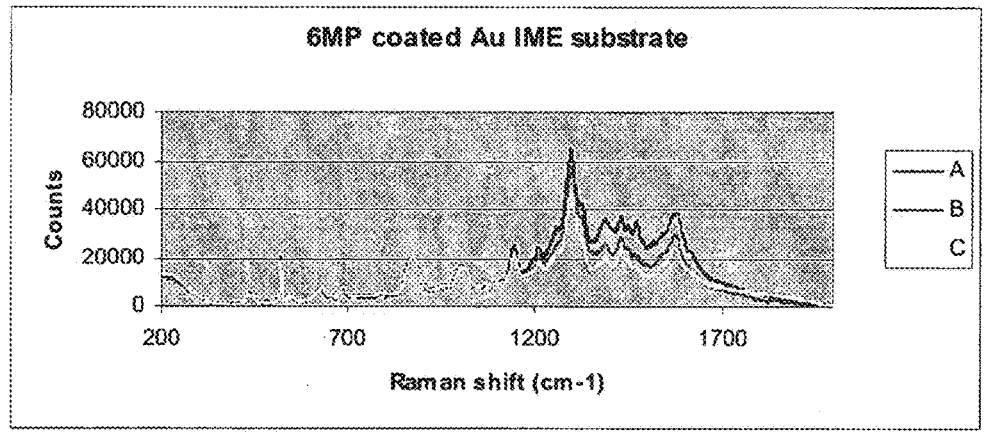
FIG. 7 shows spectra of 6-MP coated Au IME substrate taken at 10% power, 30s acquisition and 2 accumulations. The three curves represent the spectra of three measurements A, B and C.
Figure 8:
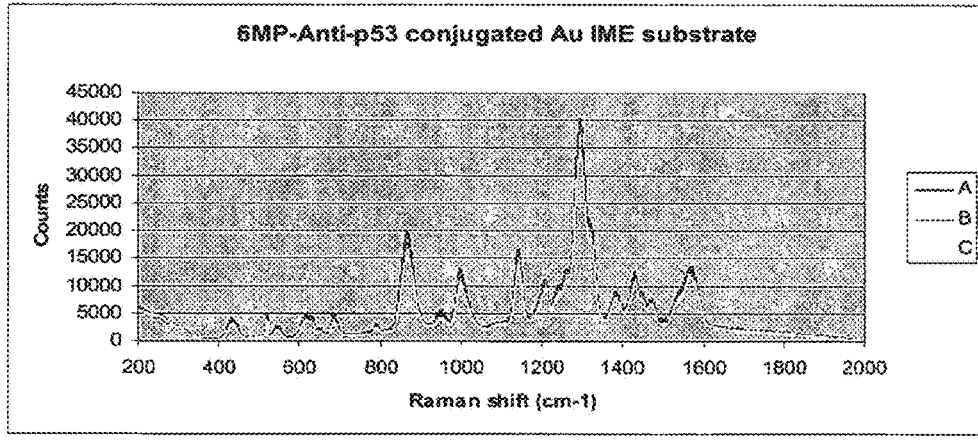
FIG. 8 shows spectra of 6-MP-anti-p53 coated Au IME substrate taken at 10% power, 30s acquisition and 2 accumulations. The three curves represent the spectra of three measurements A, B and C.
Figure 9:
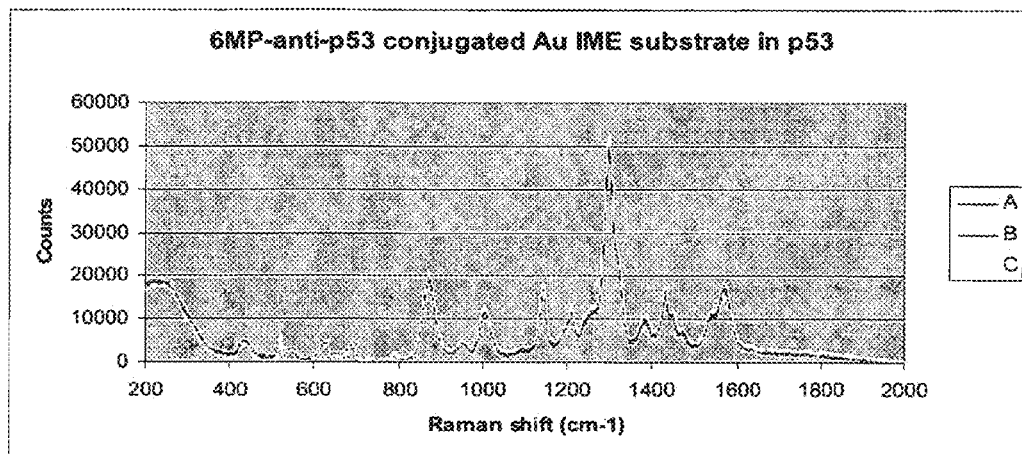
FIG. 9 shows spectra of 6-MP-anti-p53 coated Au IME substrate in presence of p53 taken at 10% power, 30s acquisition and 2 accumulations. The three curves represent the spectra of three measurements A, B and C.
Figure 10:
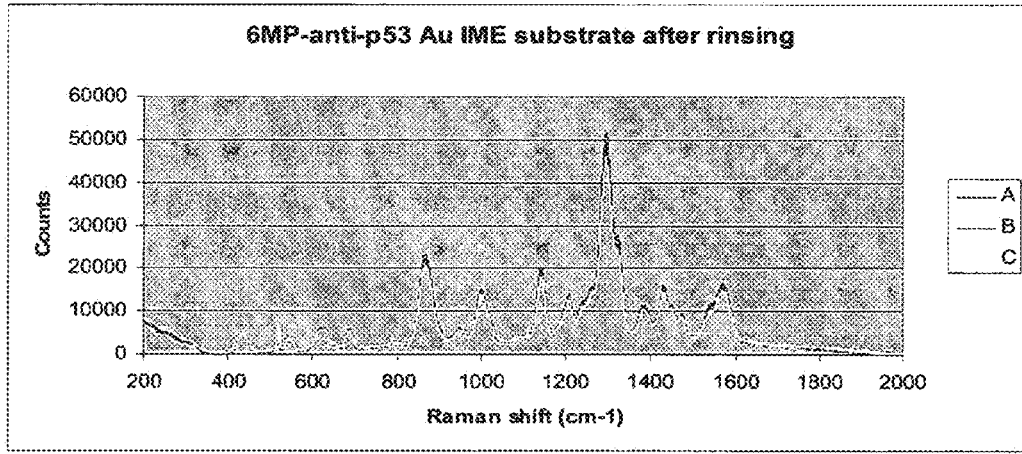
FIG. 10 shows spectra of 6-MP-anti-p53 coated Au IME substrate after rinsing taken at 10% power, 30s acquisition and 2 accumulations. The three curves represent the spectra of three measurements A, B and C.
Figure 11:
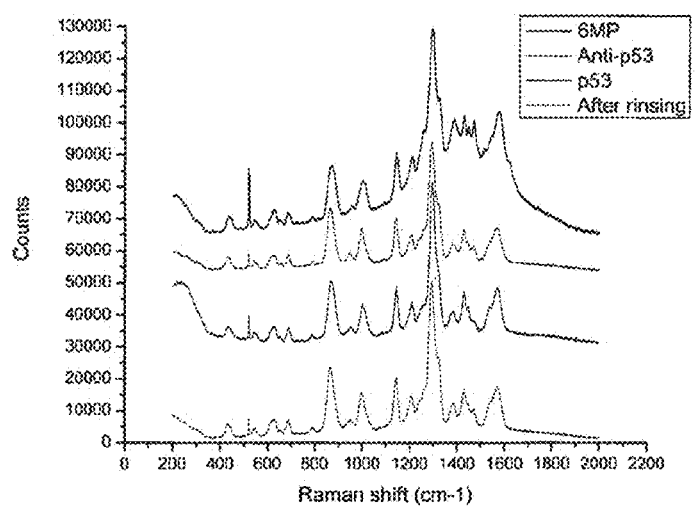
FIG. 11 shows a stacking of all "A" spectra of FIGS. 7, 8, 9 and 10. No new peaks are observed upon addition of anti-p53 and p53.
Figure 12:
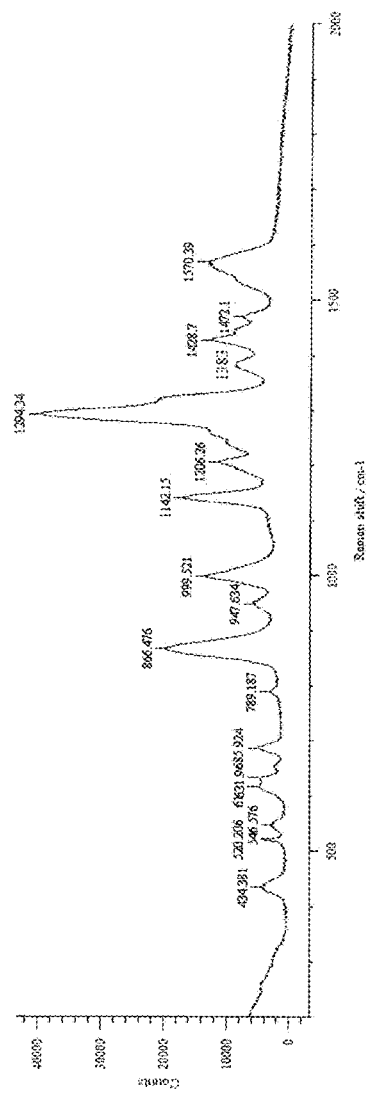
FIG. 12 shows the individual spectra of the anti-p53 conjugated biosensor of measurements a) A, b) B and c) C.
Figure 12:
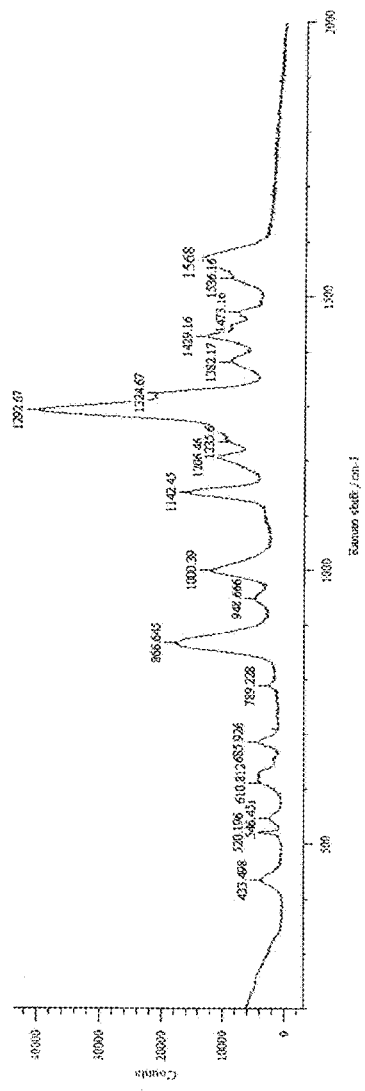
Figure 12:
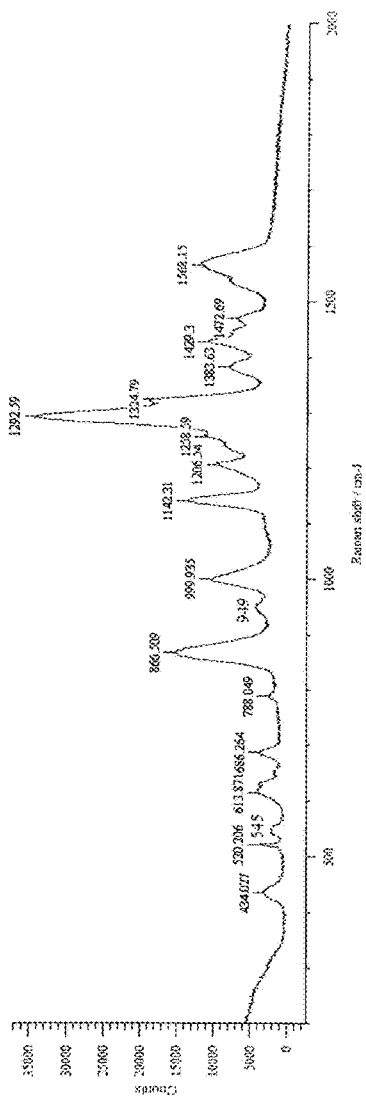
Figure 13:
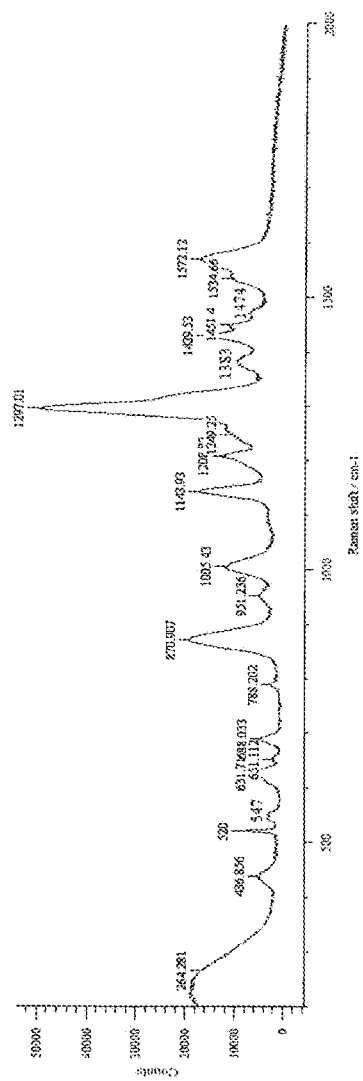
FIG. 13 shows the individual spectra of the anti-p53 conjugated and p53 incubated biosensor of measurements a) A, b) B and c) C.
Figure 13:
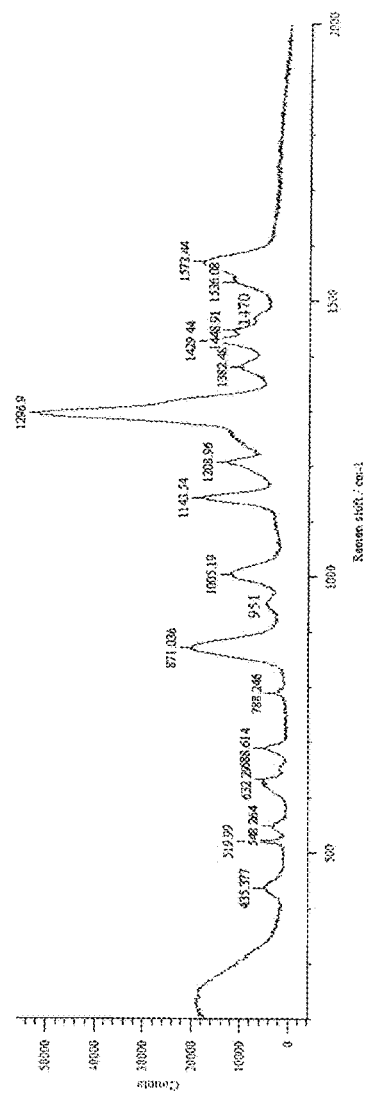
Figure 13:
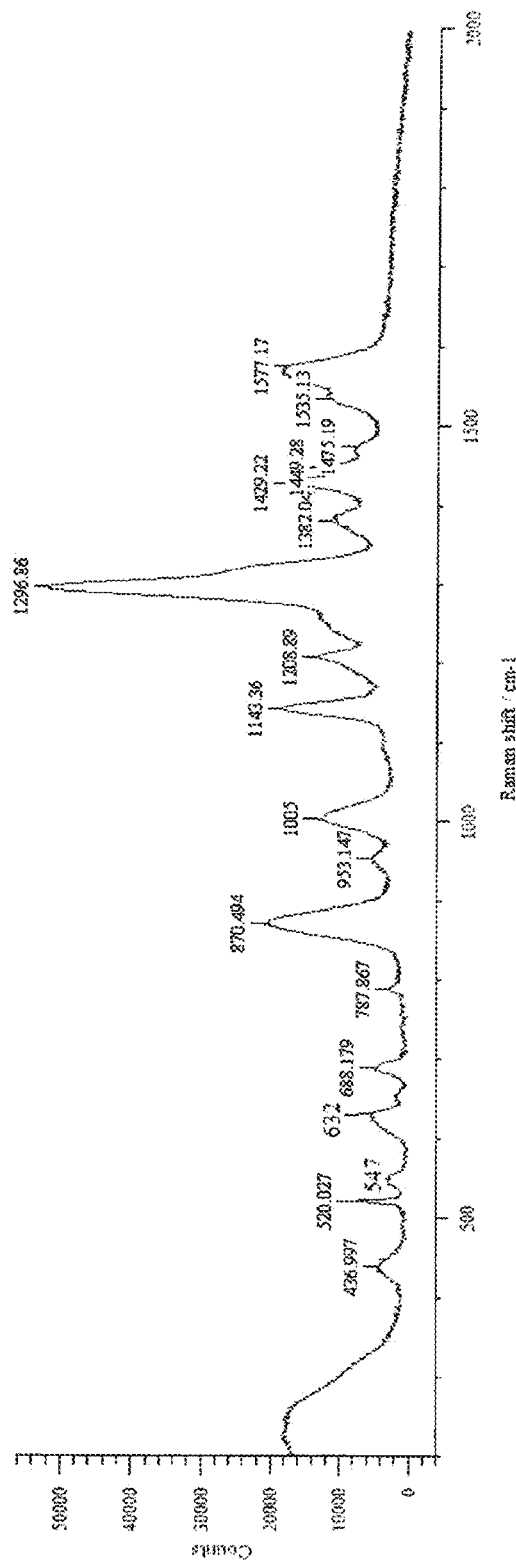
Figure 14:
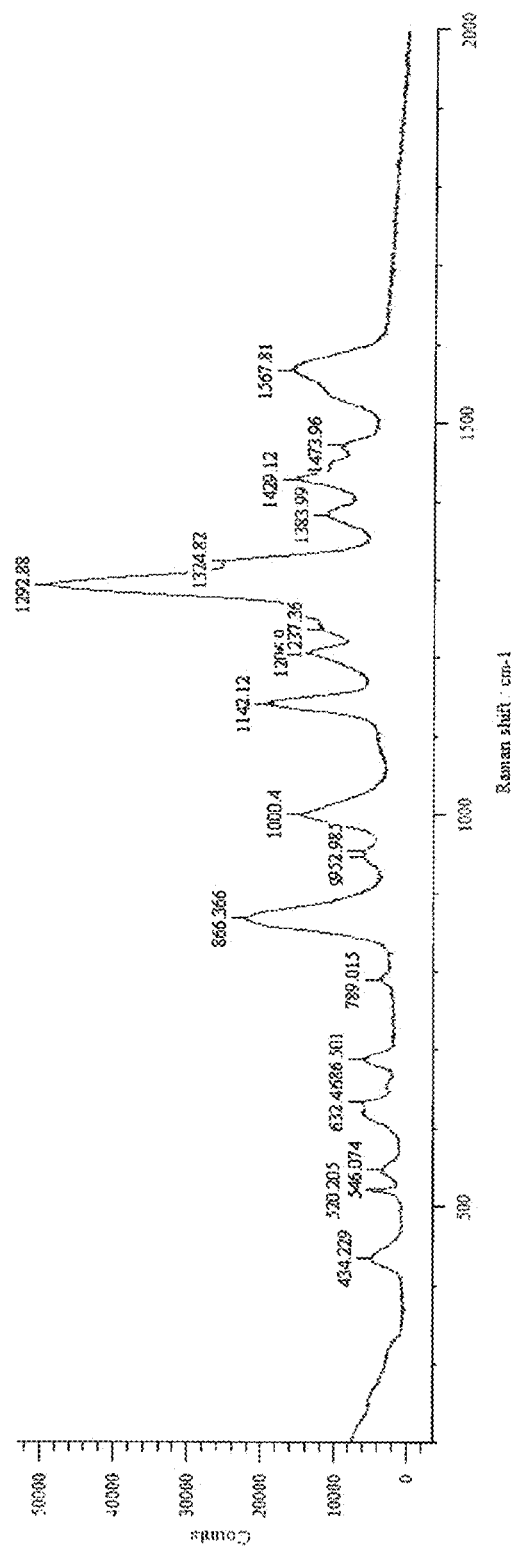
FIG. 14 shows the individual spectra of the anti-p53 conjugated and p53 incubated biosensor of measurements a) A, b) B and c) C after rinsing the biosensor with PBS.
Figure 14:
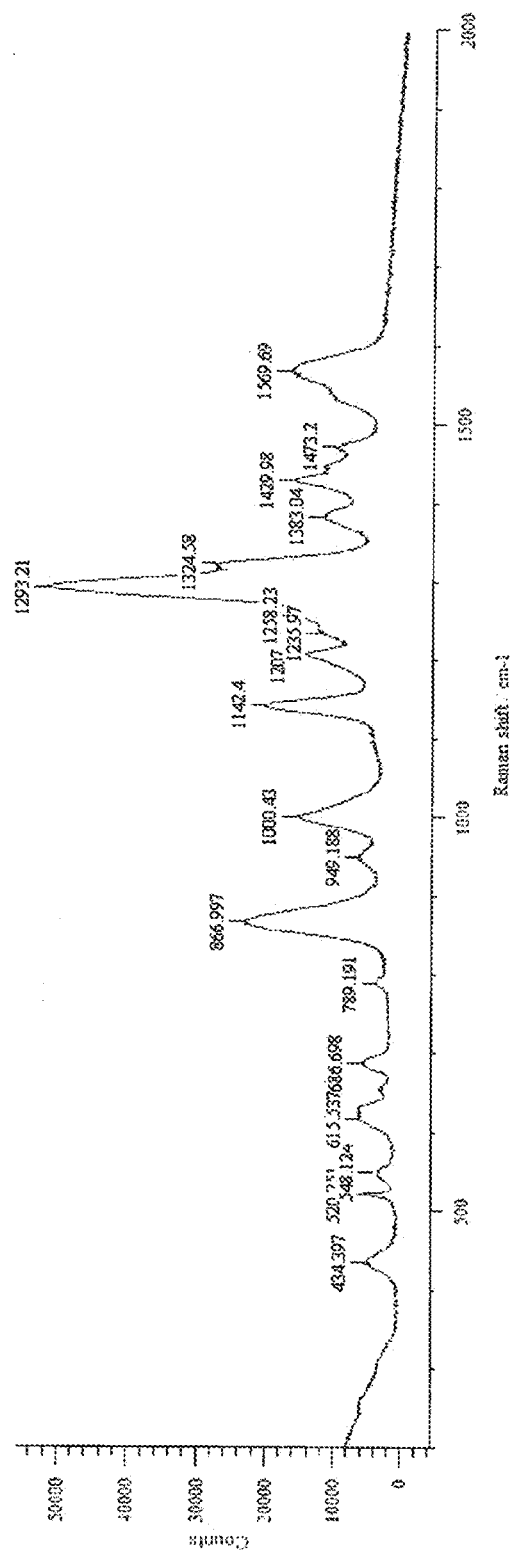
Figure 14:
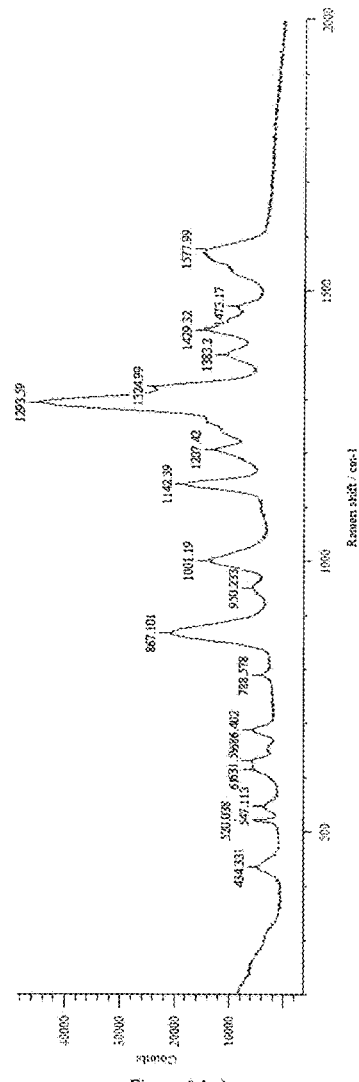
Figure 15:
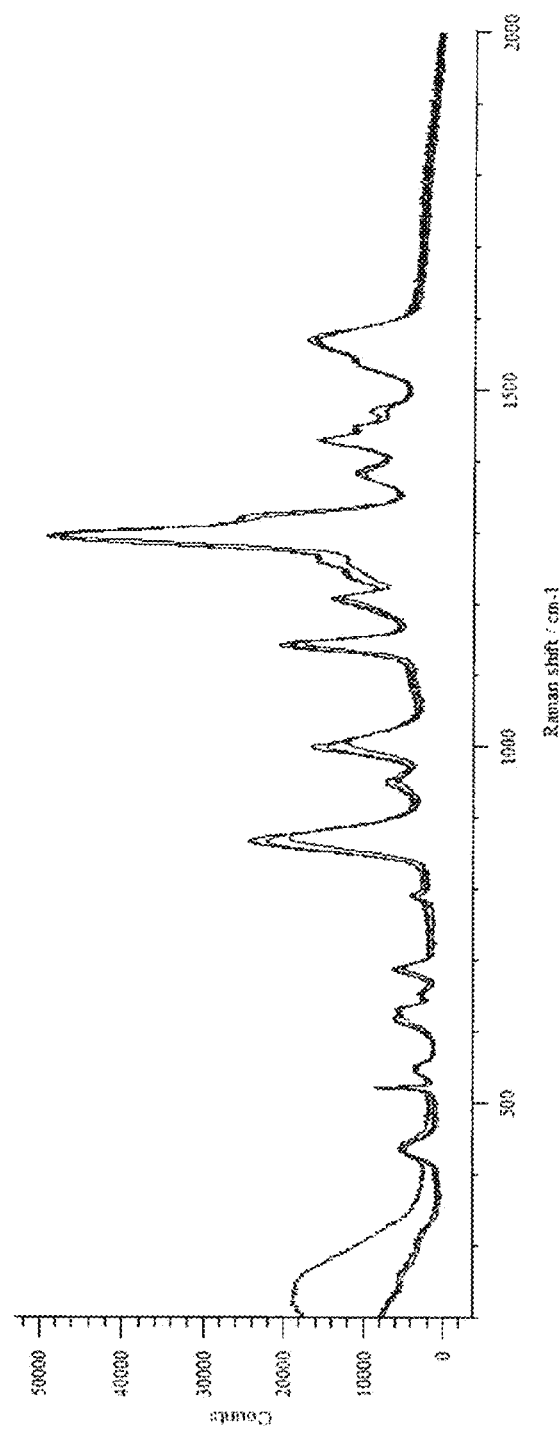
FIG. 15 shows the spectra of FIGS. 12, 13 and 14 superimposed.

The SERS measurements were repeated for clean substrate, 6-MP coated substrate, anti-p53 6-MP coated substrate in the absence and presence of p53 before and after rinsing. The clean Au IME substrate was analyzed at three spots on the sensor surface (A, B and C) using 100% power, 10s acquisition and 1 accumulation as settings. The results are shown in FIG. 6. Afterwards, the substrate was coated with 6 MP and a SERS measurement carried out with 10% power, 30s acquisition and 2 accumulations (cf. FIG. 7). In the next step, anti-p53 antibodies were conjugated to the surface via 6-MP using the EDC crosslinker. A further SERS spectral analysis of the biosensor followed, at 10% power, 30s acquisition and 2 accumulations. The results are shown in FIGS. 8 and 12, wherein FIG. 8 shows a spectra overlay plot for three measurements, whereas FIGS. 12 *a*)-*c*) show each spectrum separately and include the peak wavenumbers. Hereafter, p53 was added to the sensor and SERS spectra recoded at 10% power, 30s acquisition and 2 accumulations (cf. FIGS. 9 and 13). Then, the surface was thoroughly rinsed with deionized water and PBS was added. SERS spectra were acquired using the following parameters: 10% power, 30s acquisition and 2 accumulations. FIGS. 10 and 14 show the results of these recordings. It becomes apparent that no new peaks are observed upon addition of anti-p53 and p53 to the sensor surface. This is particularly evident in FIG. 11, which represents a cumulative plot of the spectra obtained throughout the procedure from the analysis of location A. FIG. 15 represents a cumulative plot of the spectra obtained from three measurements after antibody conjugation, addition of p53 and rinsing the sensor surface.

A large Raman shift is observed when p53 binds to the anti-p53 antibody that has been immobilized on the Au IME substrate (cf. FIG. 15). The ~866, ~947, ~1000 and ~1292 peaks, corresponding to $vC8-H+vN7-C8+vN9-C8$, $\alpha C5-N-7-C8+\delta N9-C8+\alpha C6-S$, $\alpha S-H$ and $\delta C2-H+\delta C8-H+\alpha N1-C2-N3+\delta N9-H$, show the most prominent shifts of ~4-5 cm$^{-}$. These represent bonds between 6-MP and the substrate and/or the antibody.

When the substrate is rinsed with deionized water and the Raman spectrum is taken in PBS, the spectrum closely resembles the initial spectrum before incubation with p53 (cf. FIGS. 12, 14 and 15).

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by specific embodiments and optional features, modification and variation of the inventions embodied therein herein disclosed may be resorted to by those skilled in the art, and that such modifications and variations are considered to be within the scope of this invention.

The content of all documents cited herein is incorporated by reference in their entirety.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are in the following claims. In addition, where features or aspects of the invention are described in terms of Markush groups, those skilled in the art will recognize that the invention is also thereby described in terms of any individual member or subgroup of members of the Markush group.

What is claimed is:

1. A method for detecting one or more analytes using surface enhanced Raman spectroscopy (SERS), comprising:
    contacting the one or more analytes with a conjugate, the conjugate comprising at least one analyte binding molecule attached to a metal substrate surface via a Raman-active molecular linker that enhances Raman scattering of the metal substrate and undergoes a structural change upon an analyte binding event in which the one or more analytes bind to the at least one analyte binding molecule; and
    detecting peak shifts in the surface enhanced Raman spectrum from said conjugate as an indication of the analyte binding event, wherein the peak shifts in the surface enhanced Raman spectrum of the conjugate are correlated with amount of the one or more analytes.

2. The method of claim 1, wherein the one or more analytes are selected from the group consisting of proteins, peptides, nucleic acids, carbohydrates, lipids, cells, viruses, small molecules, and haptens.

3. The method of claim 1, wherein the at least one analyte binding molecule specifically binds the one or more analytes.

4. The method of claim 3, wherein the at least one analyte binding molecule is selected from the group consisting of an antibody, an antibody fragment, and antibody-like molecules.

5. The method of claim 3, wherein the at least one analyte binding molecule is a monoclonal or polyclonal antibody.

6. The method of claim 1, wherein the method is a multiplex method for detecting more than one analyte, wherein in the contacting step more than one analyte binding molecule is used.

7. The method of claim 1, wherein the at least one analyte binding molecule is covalently coupled to the Raman-active molecular linker, wherein the Raman-active molecular linker is attached to the substrate surface via covalent interactions.

8. The method of claim 1, wherein the Raman-active molecular linker is selected from the group consisting of 6-Mercaptopurine, 8-Aza-adenine, N-Benzoyladenine, 2-Mercapto-benzimidazole, 4-Amino-pyrazole[3,4-d]pyrimidine, Zeatin, Methylene Blue, 9-Amino-acridine, Ethidium Bromide, Bismarck Brown Y, N-Benzylaminopurine, Thionin acetate, 3,6-Diaminoacridine, 6-Cyanopurine, 4-Amino-5-imidazolecarboxamidehydrochloride, 1,3-Diiminoisoindoline, Rhodamine 6G, Crystal Violet, Basic Fuchsin, Aniline Blue Diammonium salt, N-[(3-(Anilinomethylene)-2-chloro-1-cyclohexen-1-yl)methylene]anilinemonohydrochloride, O-(7-Azabenzotriazol-1-yl)-N,N,N',N'-tetramethyluroniumhexafluorophosphate, 9-Aminofluorene hydrochloride, Basic Blue, 1,8-Diamino-4,5-dihydroxyanthraquinone, Proflavine hemisulfate salt hydrate, 2-Amino-1,1,3-propenetricarbonitrile, Variamine Blue RT salt, 4,5,6-Triaminopyrimidine sulfate salt, 2-Aminobenzothiazole, Melamine, 3-(3-Pyridylmethylamino)Propionitrile, Silver(I) Sulfadiazine, Acriflavine, 4-Amino-6-mercaptopyrazole[3,4-d]pyrimidine, 2-Aminopurine, Adenine Thiol FAD Fluoroadenine, 4-Amino-6- mercapyopyrazole[3,4-d]pyrimidine, Rhodamine 110, Adenine, 5-Amino-2-mercaptobenzimidazole, Acridine Orange Hydrochloride, Cresyl Violate Acetate, Acriflavine Neutral, Dimidium Bromide, 5,10,15,20-Tetrakis(N-methyl-4-pyridinio)porphyrin Tetra(p-toluenesulfonate), 5,10,15, 20-Tetrakis(4-trimethylaminophenyl)porphyrin Tetra(p-toluenesulfonate), 3,5-Diaminoacridine Hydrochloride, Propidium Iodide (3,8-diamino-5-(3-diethylaminopropyl)-6-phenylphenanthridinium iodidemethiodide), Trans-4-[4-(dimethylamino)styryl]-1-methylpyridinium iodide, and 4-((4-(dimethylamino)phenyl)azo)benzoic acid, succinimidyl ester or derivatives thereof.

9. The method of claim 8, wherein the Raman-active molecular linker is a thiol-group containing compound.

10. The method of claim 9, wherein the Raman-active molecular linker is 6-Mercaptopurine.

11. The method of claim 1, wherein the at least one analyte binding molecule is covalently coupled to the Raman-active molecular linker by amide bond formation.

12. The method of claim 11, wherein 1-ethyl-3-(3-dimethylaminopropyl) carbodiimide is used as a coupling agent.

13. The method of claim 1, wherein the substrate is a nanoparticle.

* * * * *

UNITED STATES PATENT AND TRADEMARK OFFICE
CERTIFICATE OF CORRECTION

PATENT NO. : 9,689,801 B2
APPLICATION NO. : 13/517937
DATED : June 27, 2017
INVENTOR(S) : Kiang Wei Kho et al.

It is certified that error appears in the above-identified patent and that said Letters Patent is hereby corrected as shown below:

In the Claims

In Claim 1, at Column 18, Line 14, the text: "attached to a metal substrate surface" should be replaced with the text: -- surface of a metal substrate --.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*